United States Patent [19]

Plow et al.

[11] Patent Number: 5,149,780

[45] Date of Patent: Sep. 22, 1992

[54] PEPTIDES AND ANTIBODIES THAT INHIBIT INTEGRIN-LIGAND BINDING

[75] Inventors: Edward F. Plow; Stanley E. D'Souza; Mark H. Ginsberg, all of San Diego, Calif.

[73] Assignee: The Scripps Research Institute, La Jolla, Calif.

[21] Appl. No.: 252,674

[22] Filed: Oct. 3, 1988

[51] Int. Cl.[5] .................. C07K 7/00; C07K 15/28; C12N 15/11; C12N 15/00
[52] U.S. Cl. ........................ 530/324; 530/387.9; 530/830; 530/388.22; 530/388.7; 530/388.2; 536/27; 435/69.1; 435/69.6; 435/172.3; 435/220.1
[58] Field of Search ............... 530/300, 324, 326, 327, 530/387; 536/27; 424/85.8; 435/69.1, 69.7, 69.6, 172.3, 320.1

[56] References Cited

PUBLICATIONS

Calvete et al., Abstract, (1991), Biochem. J. 274, 457–464.
Alberts et al., "Molecular Biology of the Cell", Garland Publishing, Inc., New York (1983).
Calvete et al. (1988), Tryptic Digestion of Human GPIIIa. Biochem. J. 250, 697–704.
Fitzgerald et al. (1987) Protein Sequence of Endothelial Glycoprotein IIIa Derived from a cDNA clone. J. Biol. Chem. 262, 3936–3939.

Primary Examiner—Robert A. Wax
Assistant Examiner—R. Keith Baker
Attorney, Agent, or Firm—Douglas A. Bingham

[57] ABSTRACT

Polypeptides which are derived from the Arg-Gly-Asp (RGD) binding portion of an Integrin beta subunit are disclosed as are their use for modulation of Integrin ligand binding. Anti-antibody peptides, hybridomas secreting these antibodies, as well as methods of making any using such antibodies, and recombinant DNA molecules that define the structural gene coding for the polypeptides are also contemplated within the scope of the present invention.

12 Claims, 6 Drawing Sheets

```
      GGGCCCAACATCTGTACCACGCGAGGTGTGAGCTCCTGCCAGCAGTGCCTGGCTGTGAGC    158
  1   G  P  N  I  C  T  T  R  G  V  S  S  C  Q  Q  C  L  A  V  S

CCCATGTGTGCCTGGTGCTCTGATGAGGCCCTGCCTCTGGGCTCACCTCGCTGTGACCTG    218
 21   P  M  C  A  W  C  S  D  E  A  L  P  L  G  S  P  R  C  D  L

AAGGAGAATCTGCTGAAGGATAACTGTGCCCCAGAATCCATCGAGTTCCCAGTGAGTGAG    278
 41   K  E  N  L  L  K  D  N  C  A  P  E  S  I  E  F  P  V  S  E

GCCCGAGTACTAGAGGACAGGCCCCTCAGCGACAAGGGCTCTGGAGACAGCTCCCAGGTC    338
 61   A  R  V  L  E  D  R  P  L  S  D  K  G  S  G  D  S  S  Q  V

ACTCAAGTCAGTCCCCAGAGGATTGCACTCCGGCTCCGGCCAGATGATTCGAAGAATTTC    398
 81   T  Q  V  S  P  Q  R  I  A  L  R  L  R  P  D  D  S  K  N  F

TCCATCCAAGTGCGGCAGGTGGAGGATTACCCTGTGGACATCTACTACTTGATGGACCTG    458
101   S  I  Q  V  R  Q  V  E  D  Y  P  V  D  I  Y  Y  L  M  D  L

TCTTACTCCATGAAGGATGATCTGTGGAGCATCCAGAACCTGGGTACCAAGCTGGCCACC    518
121   S  Y  S  M  K  D  D  L  W  S  I  Q  N  L  G  T  K  L  A  T

CAGATGCGAAAGCTCACCAGTAACCTGCGGATTGGCTTCGGGGCATTTGTGGACAAGCCT    578
141   Q  M  R  K  L  T  S  N  L  R  I  G  F  G  A  F  V  D  K  P

GTGTCACCATACATGTATATCTCCCCACCAGAGGCCCTCGAAAACCCCTGCTATGATATG    638
161   V  S  P  Y  M  Y  I  S  P  P  E  A  L  E  N  P  C  Y  D  M

AAGACCACCTGCTTGCCCATGTTTGGCTACAAACACGTGCTGACGCTAACTGACCAGGTG    698
181   K  T  T  C  L  P  M  F  G  Y  K  H  V  L  T  L  T  D  Q  V

ACCCGCTTCAATGAGGAAGTGAAGAAGCAGAGTGTGTCACGGAACCGAGATGCCCCAGAG    758
201   T  R  F  N  E  E  V  K  K  Q  S  V  S  R  N  R  D  A  P  E

GGTGGCTTTGATGCCATCATGCAGGCTACAGTCTGTGATGAAAAGATTGGCTGGAGGAAT    818
221   G  G  F  D  A  I  M  Q  A  T  V  C  D  E  K  I  G  W  R  N
```

FIG. 1

ALIGNMENT OF RGD CROSSLINKED SITE WITH OTHER INTEGRINS

| | | | | | |
|---|---|---|---|---|---|
| Cytoadhesin: (GPIIIa) | DYPvDiYYLM DLSYSMKDDL | wsiqnLGTkL atqMrklTSn | lRIGFGaFVd KpvSPymYIS | ppe |
| LeuCam: | gYPIDLYYLM DLSYSMlDDL | rNVKkLGgdL lralneITes | gRIGFGSFvd KTVlPfvn.. | ThP |
| VLA: | DYPIDLYYLM DLSYSMKDDL | eNVKsLGTdL mneMrrITSd | fRIGFGSFVe KTVmP..YIS | TtP |
| Integrin: Avian | DYPIDLYYLM DLSYSMKDDL | eNVKsLGTaL mreMekITSd | fRIGFGSFve KTVmP..YIS | TtP |
| Integrin: Xenopus | DYPIDLYYLM DLSfSMKDDL | eNVKsLGTaL mteMekITSd | fRIGFGSFve KTVmP..YIS | TtP |
| Consensus: | DYPIDLYYLM DLSYSMKDDL | -NVK-LGT-L ---M---ITS- | -RIGFGSFV- KTV-P---YIS | T-- |

FIG. 6

PEPTIDES AND ANTIBODIES THAT INHIBIT INTEGRIN-LIGAND BINDING

TECHNICAL FIELD

The present invention relates to a polypeptide derived from the Arg-Gly-Asp (RGD) binding region of the Integrin beta subunit and to the use of that polypeptide to modulate Integrin-ligand binding. Also contemplated are antibodies that immunoreact with the RGD-binding region of an Integrin beta subunit and the use of those antibodies to modulate or detect Integrin-ligand binding or detect ligand binding sites within Integrins.

BACKGROUND

Cell adhesion generally involves recognition of specific adhesive proteins by cell surface receptors. A family of cell surface receptors of particular interest to the present invention are the Integrins.

According to Hynes, Cell, 48:549-554 (1987), Integrins are a functionally and structurally related group of receptors that interact with a wide variety of ligands including extracellular matrix glycoproteins, complement and other cells. Integrins participate in cell-matrix and cell-cell adhesion in many physiologically important processes including embryological development, hemostasis, thrombosis, wound healing, immune and nonimmune defense mechanisms and oncogenic transformation. Two human genetic diseases, Glazmann's thrombasthenia and leukocyte adhesion deficiency, affect members of the Integrin family.

Structurally, Integrins are heterodimeric complexes comprised of noncovalently associated alpha and beta subunits. Within the Integrin family there are recognized subfamilies related by the presence of a similar beta subunit and members within each group are distinguished by unique alpha subunits.

For instance, recent evidence indicates that an Integrin found on the surface of platelets and known as GPIIb-IIIa is one of several adhesion receptors that have unique alpha subunits but share a similar beta subunit and the functional property of recognizing the tripeptide amino acid residue sequence Arg-Gly-Asp (using single letter symbols, RGD). Pytela et al., Science. 231:1559-1562 (1986) and Ruoslahti et al., Cell, 44:517-518 (1986). In addition to GPIIb-IIIa, this group of related receptors includes the vitronectin receptor (VnR) and fibronectin receptor (FnR) isolated from osteosarcoma cells. [Pytela et al., Cell. 40:191-198 (1985), and Pytela et al., Proc. Natl. Acad. Sci. U.S.A., 82:5766-5770 (1985).

The similar functional, structural, and antigenic properties of these proteins suggests GPIIb-IIIa and VnR are members of an Integrin subfamily for which the designation "cytoadhesin" has been proposed. Plow et al., Proc. Natl. Acad. Sci. U.S.A., 83:6002-6006 (1986). Within the cytoadhesin group, distinct alpha subunits combine with a common or very similar beta subunit, resulting in functionally distinguishable receptors. Ginsberg et al., J. Biol. Chem., 262:5437-5440 (1987).

For example, GPIIb-IIIa is a heterodimer complex comprised of alpha and beta subunits. Jennings et al., J. Biol. Chem., 257:10458-10466 (1982). The alpha subunit, GPIIb, consists of a heavy chain and a light chain that are linked together by disulfide bonds. The beta subunit, GPIIIa is a single chain polypeptide of about 100 kDa. Phillips et al., J. Biol. Chem.. 252:2121-2126 (1977). Cell surface molecules immunologically related to GPIIb-IIIa have been identified on a variety of cell types. See Thiagarajan et al., J. Clin. Invest., 75:896-901 (1985); Plow et al., Proc. Natl. Acad. Sci. U.S.A., 83:6002-6006 (1986); and Fitzgerald et al., J. Biol. Chem.. 260:10893-10896 (1985).

GPIIb-IIIa contributes to platelet function through interactions with RGD-containing proteins, i.e., proteins containing an Arg-Gly-Asp amino acid residue sequence, such as fibrinogen [Bennett et al., Proc. Natl. Acad. Sci. U.S.A., 80:2417-2421 (1983)], fibronectin [Ginsberg et al., J. Clin. Invest., 71:619-624 (1983)], and von Willebrand factor [Ruggeri et al., Proc. Natl. Acad. Sci. U.S.A., 79:6038-6041 (1982)], and therefore is a component of the common platelet adhesive protein receptor [Pytela et al., Science. 231:1559-1562 (1986) and Plow et al., J. Biol. Chem., 259:5388-5391 (1984)].

At least 2 other groups of heterodimeric adhesion receptors have been identified in which a common beta subunit combines with a number of distinct alpha subunits. One group is found on leukocytes and has been referred to as the leukocyte adhesion (LeuCam) family and includes LFA-1, Mac-1, and P150,95. Sanchez-Madrid et al., J. Exp. Med.. 158:1785-1803 (1983) and Springer et al., Ciba. Found. Symp., 118:102-126 (1986). The other group is more widely distributed and has been referred to as the VLA family. Hemler et al., J. Biol. Chem., 262:3300-3309 (1987). The beta subunit of the VLA family [Hemler et al., J. Biol. Chem., 262:3300-3309 (1987)] in the chicken has been cloned, sequenced and designated "Integrin" Tamkun et al., Cell, 46:271-282 (1986)]. The sequence of chicken Integrin is similar to that of GPIIIa [Fitzgerald et al., J. Biol. Chem.. 262:3936-3939 (1987)] and to the beta subunit of the leukocyte adhesion family [Kishimoto et al., Cell, 48:681-690 (1987)]. Moreover, partial sequences of several alpha subunits also indicate similarities. Ginsberg et al., J. Biol. Chem.. 262:5437-5440 (1987); Suzuki et al., Proc. Natl. Acad. Sci. U.S.A.. 83:8614-8618 (1986); and Charo et al., Proc. Natl. Acad. Sci. U.S.A. 83:8351-8356 (1986).

The sites on GPIIb-IIIa, or the other cytoadhesins, that are crucial for their functions as adhesion receptors are presently unknown. Several observations suggest that a functionally significant site on GPIIb-IIIa is near the epitope defined by the monoclonal antibody PMI-1. This antibody binds to the heavy chain of GPIIb [Shadle et al., J. Cell. Biol. 99:2056-2060 (1984)] and defines a region of GPIIb that is associated with several distinct functional activities. For instance, PMI-1 inhibits adhesion of washed platelets to collagen. Shadle et al., J. Cell. Biol. 99:2056-2060 (1984).

BRIEF SUMMARY OF THE INVENTION

The invention relates to polypeptides [herein also referred to as subject polypeptide(s)] of about 60 to about 90 amino acid residues in length which are characterized as having an amino acid residue sequence homologous to the RGD-binding portion of an Integrin beta subunit.

The invention also relates to a polyclonal antibody which immuno reacts with a subject polypeptide as well as monoclonal antibodies that immunoreact with an epitope formed by the RGD-binding region of an Integrin beta subunit.

Also contemplated within the scope of the present invention are the hybridomas having the capacity to produce a subject monoclonal antibody.

Methods of modulating the adhesion, in vivo, of cells expressing an Integrin beta subunit to which the subject polypeptides correspond.

Further contemplated is a nucleotide segment comprising no more than about 12,000 nucleotide base pairs including sequence defining a structural gene coding for a subject polypeptide. Also contemplated is a recombinant DNA molecule comprising a vector operatively linked to a DNA segment that defines a structural gene coding for a subject polypeptide.

Methods of modulating cell adhesion using the polypeptides and antibodies of the present invention are also contemplated.

BRIEF DESCRIPTION OF THE DRAWINGS

FIG. 1 illustrates the nucleotide base sequence and deduced amino acid residue sequence of a DNA segment coding for the RGD-binding region of GPIIIa. Amino acid residue and nucleotide base positions are indicated in the left and right margins, respectively. Fitzgerald et al., J. Biol. Chem., 262:3936–3939 (1987).

Lanes 2 and 4 are the intact GPIIIa:Fn-7 complexes from thrombin stimulated and nonstimulated cells, respectively.

Lanes 3 and 5 are the V8 protease (2 mg/ml) digests from stimulated and nonstimulated cells, respectively.

For lanes 6 and 7, GPIIIa:Fn-7 was extracted from the gel slices in 2% SDS, 0.2 M Tris, pH 7.8, precipitated with 80% acetone, and then digested with chymotrypsin. Lane 6 is intact GPIIIa:Fn-7. Lane 7 is after digestion with 20 μg chymotrypsin for 1 hr at 22° C. Note that no bonds within the peptide are susceptible to V8 protease. If the tyrosyl-glycyl peptide bond within $^{125}$I-Fn-7 were cleaved by chymotrypsin, the radioactivity on the tyrosine residue would remain crosslinked to GPIIIa via the lysine residue.

Figure 3:
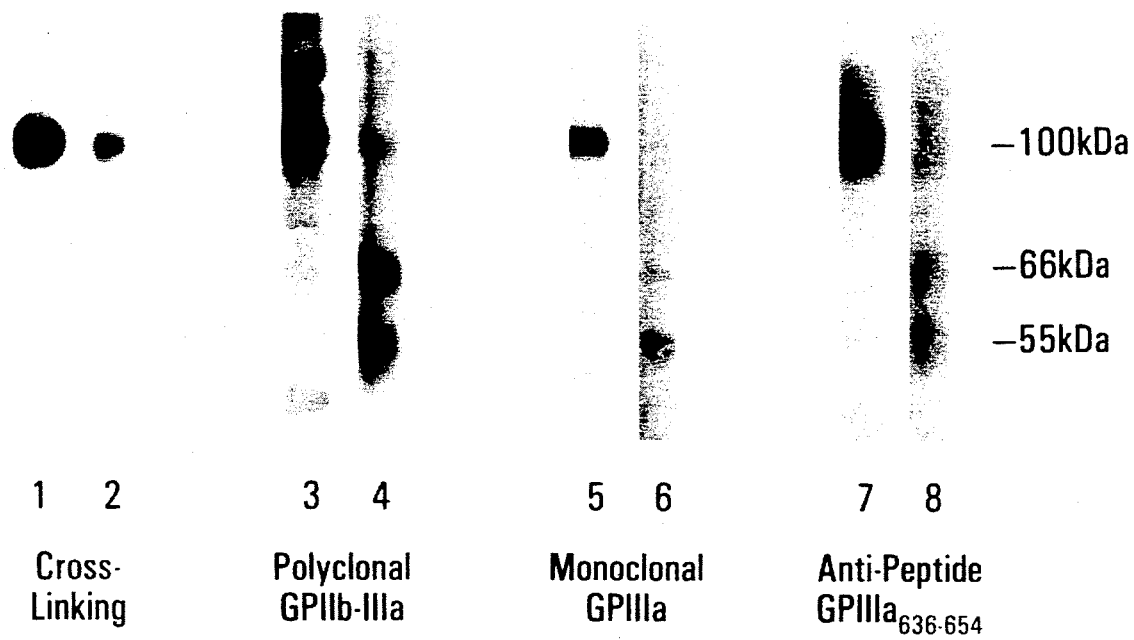

FIG. 3 illustrates the RGD crosslinking site resides in the 34 kDa NH$_2$-terminal portion of the beta subunit (GPIIIa). $^{125}$I-Fn-7 was crosslinked to platelets, and the intact cells were then digested with chymotrypsin (0.5 mg/ml for 4 hours at 22° C.). The cells were recovered by centrifugation and analyzed on SDS-PAGE (10% gels under nonreducing conditions).

Lanes 1 and 2 show the position of the $^{125}$I-Fn-7 peptide crosslinked to platelets based upon autoradiography without and with chymotrypsin digestion, respectively. Lanes 3–8 are immunoblots of these platelets after transfer onto PVDF membranes. Lanes 3, 5 and 7 are from undigested platelets, and Lanes 4, 6 and 8 are from chymotrypsin-digested platelets. The immunoblots, developed with horseradish peroxidase conjugates, were probed with polyclonal antibody to GPIIb-IIIa (lanes 3–4), a monoclonal antibody (22C4) to GPIIIa [Ginsberg et al., J. Biol. Chem. 262:5437 (1987)], (lanes 5 and 6) and an anti-peptide antibody made to a region (amino acid residues 636–654) in the COOH-terminal aspects of GPIIIa (lanes 7 and 8).

Figure 2:
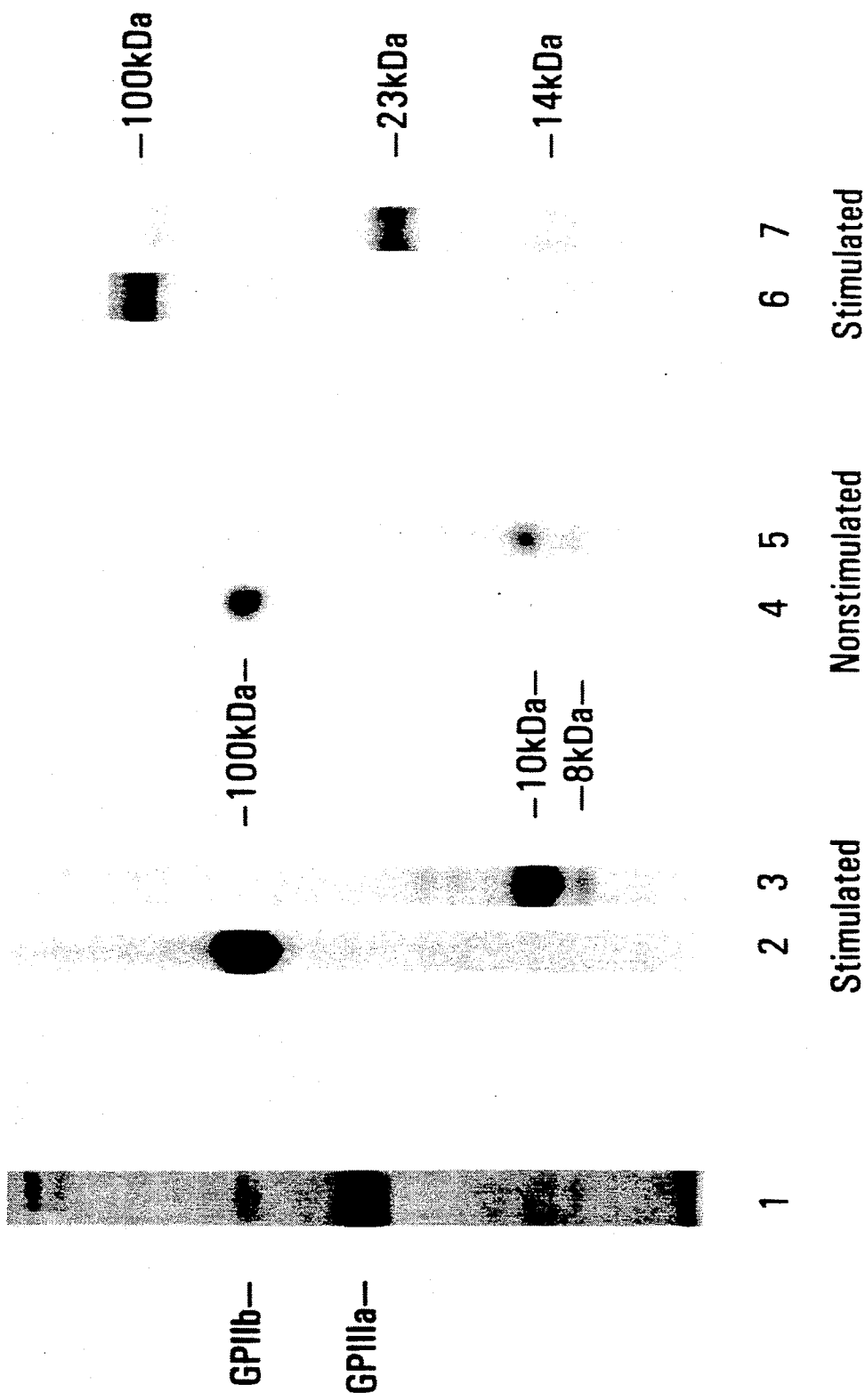
FIG. 2 illustrates the results of the crosslinking of an RGD peptide to discrete sites in the beta subunit (GPIIIa) of an Integrin adhesion receptor. The $^{125}$I-labeled RGD peptide, Fn-7 (20 μM), was bound to platelet ($6 \times 10^8$/ml) for 45 min at 22° C., and crosslinked with $BS^3$ (0.2 mM). The fragmentation patterns after proteolysis were analyzed by SDS-PAGE [Laemmli, Nature. 227:680 (1970)] and autoradiography. Lane 1, a typically SDS-PAGE analysis (7.5% gel, nonreducing conditions), showing the predominance of $^{125}$I-Fn-7 crosslinking to the beta subunit (GPIIIa) and its more minor crosslinking to the alpha subunit (GPIIb) on thrombin-stimulated platelets. Lanes 2–7, GPIIIa:Fn-7 bands were excised from gels, subjected to proteolysis and then analyzed by SDS-PAGE (15% gels, reducing conditions). For lanes 2–5, GPIIIA:Fn-7 bands were excised and digestions with V-8 protease were performed within the gel slices as described in Cleveland et al., J. Biol. Chem. 252:1102 (1977).
Figure 4:
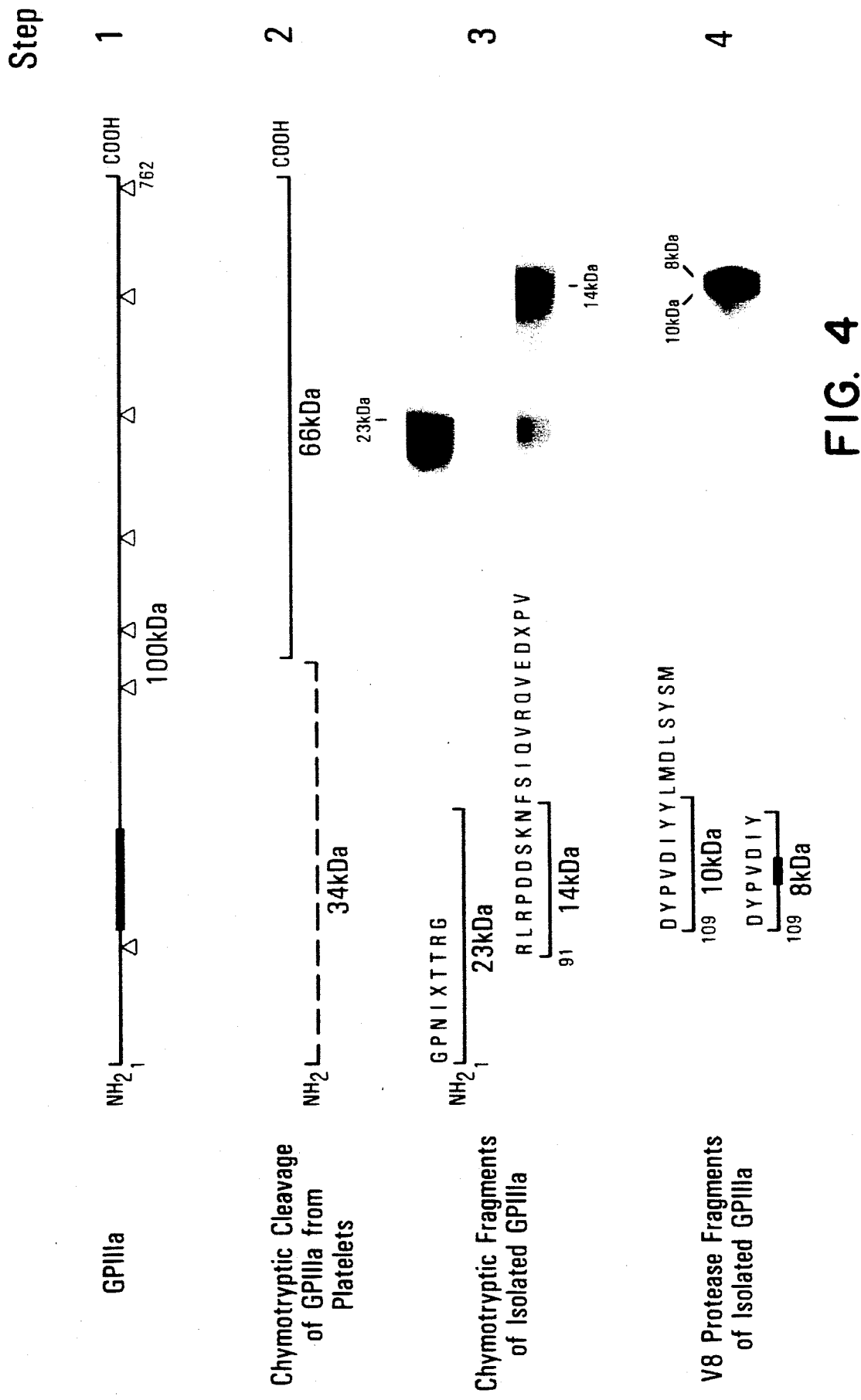

FIG. 4 illustrates localization of the RGD crosslinking site within the bet subunit (GPIIIa). The diagram illustrates the various proteolytic fragments of the GPIIIa:Fn-7 isolated, their determined NH$_2$-terminal amino acid sequences and their location within the known structure of GPIIIa. In step 2, the NH,-terminal 34 kDa localization is based upon the chymotryptic cleavage of intact platelets (See FIG. 2). GPIIIa:Fn-7 was extracted from gels and concentrated as indicated in FIG. 2. GPIIIa:Fn-7 was solubilized in 1% SDS, PBS, pH 7.3, and then digested with chymotrypsin at a 1:1 (w/w) substrate/enzyme ratio for 24 h at 22° C. Samples were boiled to inactivate the enzyme, and then applied to a C-18 HPLC reverse phase column, equilibrated in 0.1% trifluoroacetic acid and 10 μM dithiothreitol. The peptides were eluted with an acetonitrile gradient containing 0.08% trifluoroacetic acid and 10 μM dithiothreitol. Radioactive peaks were pooled, concentrated and separated on SDS-PAGE using a 15% gel under reducing conditions. The gels were transferred to PVDF membranes as described for sequence analyses [Matsudaira, J. Biol. Chem. 262:10035 (1987)] and then autoradiographed. Radioactive bands, at 23 and 14 kDa from the chymotryptic digest (Step 3) and 10 and 8 kDa from the V8 protease digest (Step 4) were excised and subjected to NH-terminal sequence analysis in an Applied Biosystem Model 475A gas-phase sequenator. The sizes of the fragments and the position of the NH$_2$-terminal residues of each gragment are drawn to scale relative to GPIIIa. The open triangles represent potential glycosylation sites, X in amino acid sequences indicate undetermined residues, and the heavy bar indicates the location of RGD crosslinking region.

Figure 5:
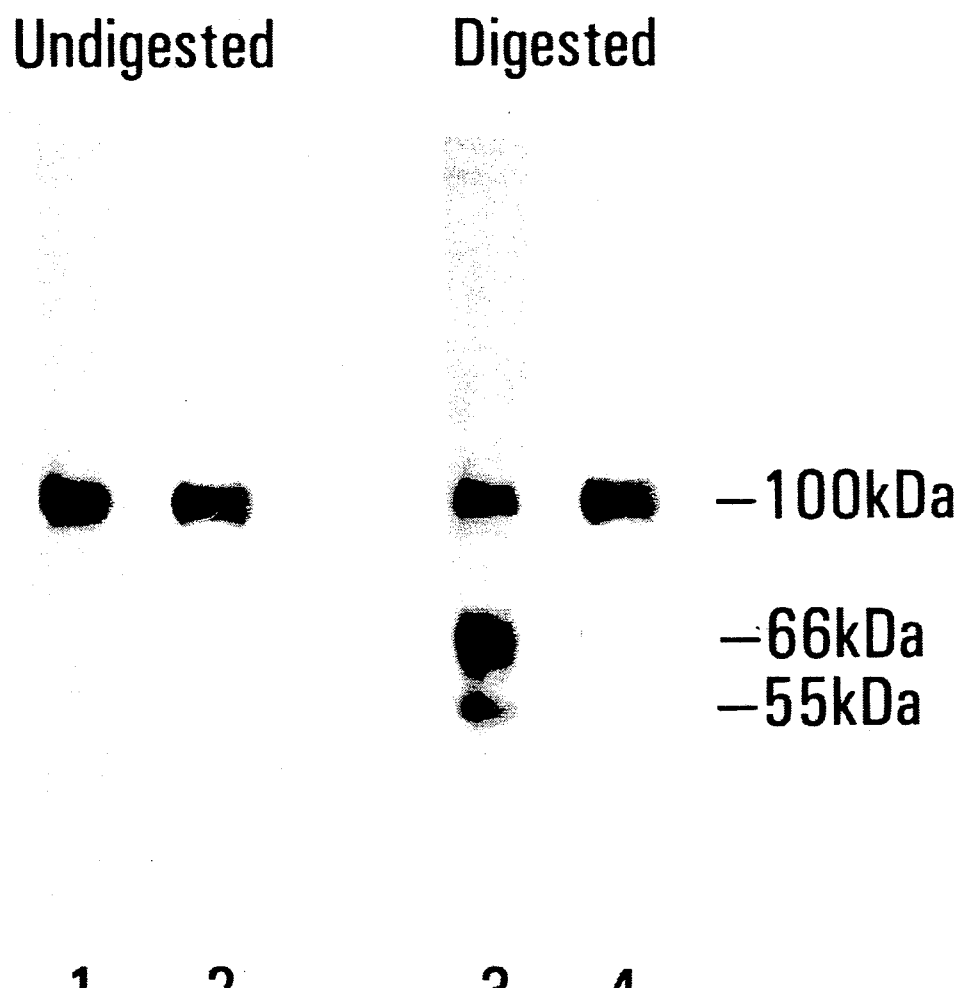

FIG. 5 illustrates the results obtained by RGD-affinity chromatography of platelets incubated in the absence (lanes 1 & 2) and presence lanes 3 & 4 of chymotrypsin. After incubation, the platelets were solubilized in octylglucoside, and passed over an RGD-affinity column substantially as described in Pytela et al., Science, 231:1559 (1986) and Lam et al., J. Biol. Chem., 262:947 (1987). The pass-through (lanes 1 & 3) and the bound material (lanes 2 & 4) were analyzed on SDS-PAGE (7% gels, non-reducing conditions). Gels were transferred to PVDF membranes and then probed with anti-GPIIIa monoclonal antibody 22C4.

FIG. 6 illustrates the deduced amino acid residue sequences taken from references Fitzgerald et al., J. Biol. Chem., 262:3926 (1987), Kishimoto et al., Cell. 48:681 (1987), Argraves et al, J. Cell Biol. 105:1183 (1987), Tamkun et al., Cell. 46:271 (1986), and DeSimone et al., J. Biol. Chem. 263:5333 (1988) and are aligned by the GAP and PRETTY computer program. Devereux et al., University of Wisconsin, Sequence Analysis Software Package 1987. The consensus sequence requires exact matches of at least four of the five sequences compared.

DETAILED DESCRIPTION OF THE INVENTION

A. Definitions

Amino Acid: All amino acid residues identified herein are in the natural L-configuration. In keeping with standard polypeptide nomenclature, *J. Biol. Chem.*, 243:3557-59, (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Try | L-tryptophan |
| R | Arg | L-arginine |
| D | Asp | L-aspartic acid |
| N | Asn | L-asparagine |
| C | Cys | L-cysteine |

It should be noted that all amino acid residue sequences are represented herein by formulae whose left to right orientation is in the conventional direction of amino-terminus to carboxy-terminus.

Polypeptide and Peptide: Polypeptide and peptide are terms used interchangeably herein to designate a linear series of no more than about 90 amino acid residues connected one to the other by peptide bonds between the alpha-amino and carboxy groups of adjacent residues.

Nucleoside and Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide.

Base Pair (bp): A hydrogen-bonded partnership of adenine (A) with thymine (T), or of cytosine (C) with guanine (G) in a double stranded DNA molecule.

Receptor: Receptor and receptor protein are terms used herein to indicate a biologically active proteinaceous molecule that specifically binds to (or with) other molecules.

Ligand: Ligand refers to a molecule that contains a structural portion that is bound by specific interaction with a particular receptor protein.

B. Polypeptides

A polypeptide of the present invention has at least about 60, and no more than about 90, amino acid residues. In addition, a subject polypeptide is characterized as having an amino acid residue sequence homologous to, i.e., derived from functional region as, the RGD-binding region of GPIIIa between and including residues 110-170 as shown in FIG. 1.

In preferred embodiments, a subject polypeptide has an amino acid residue sequence that corresponds, and is preferably identical to, a formula shown in Table 1.

TABLE 1

| Formula Designation | Amino Acid Residue Sequence |
|---|---|
| p1 | DYPVDIYYLMDLSYSMKDDLWSIQVNLGTKL-ATQMRKLTSNLRIGFGAFVDKPVSPYMYISPPE |
| p2 | DYPIDLYYLMDLSYSMKDDLENVKSLGTDL-MNEMRRITSDFRIGFGSFVEKTVMPYISTTP |
| p3 | GYPIDLYYLMDLSYSMLDDLRNVKKLGGDL-LRALNEITESGRIGFGSFVDKTVLPFVNTHP |

In preferred embodiments a subject polypeptide is further characterized by its ability to competitively inhibit Integrin mediated cell adhesion such as the aggregation of platelets, the adhesion of fibroblasts to a matrix, and the like.

Amino acid residues present in a subject polypeptide, in addition to a sequence corresponding to an above described formula, can be any residues that do not materially affect the basic and novel characteristics of a polypeptide as are discussed herein. Such additional residues are usually added to one or both termini of an enumerated peptide and can include repeats and partial repeats of an enumerated peptide sequence or contiguous residues of the Integrin beta subunit protein sequence.

A subject polypeptide has an amino acid residue sequence that corresponds to a RGD-binding portion of an Integrin beta subunit sequence. Thus, a polypeptide of the present invention need not be identical to the amino acid residue sequence of the RGD-binding portion of an Integrin beta subunit, so long as it is able to competitively inhibit Integrin binding to a native ligand i.e., a ligand to which the Integrin binds in vivo. Therefore, a subject polypeptide can be subject to various changes, such as insertions, deletions and substitutions, either conservative or non-conservative, where such changes provide for certain advantages in their use.

Conservative substitutions are those where one amino acid residue is replaced by another, biologically similar residue. Examples of conservative substitutions include the substitution of one hydrophobic residue such as isoleucine, valine, leucine or methionine for another, or the substitution of one polar residue for another such as between arginine and lysine, between glutamic and aspartic acids or between glutamine and asparagine and the like. The term "conservative substitution" also includes the use of a substituted amino acid in place of an unsubstituted parent amino acid provided that such a polypeptide also displays the requisite binding activity.

When a polypeptide of the present invention has a sequence that is not identical to the sequence of an Integrin beta subunit because one or more conservative or non-conservative substitutions have been made, usually no more than about 20% and more usually no more than 10% of the amino acid residues are substituted. An exception is where additional residues have been added at either terminus for the purpose of providing a "linker" by which the polypeptides of this invention can be conveniently affixed to a label or solid matrix, or antigenic carrier. Labels, solid matrices and carriers that can be used with the polypeptides of this invention are described hereinafter.

Amino acid residue linkers are usually at least one residue and can be 40 or more residues, more often 1 to 10 residues. Typical amino acid residues used for linking are tyrosine, cysteine, lysine, glutamic and aspartic acid, or the like. In addition, a polypeptide sequence of this invention can differ from the natural sequence by the sequence being modified by terminal-$NH_2$ acylation, e.g., acetylation, or thioglycolic acid amidation, terminal-carboxlyamidation, e.g., ammonia, methylamine, etc.

When coupled to a carrier via a linker to form what is known in the art as a carrier-hapten conjugate, a subject polypeptide is capable of inducing antibodies that immunoreact with the Integrin beta subunit to which the amino acid residue sequence of the polypeptide corresponds. In view of the well established principle of immunologic cross-reactivity, the present invention therefore contemplates antigenically related variants of a polypeptide having an amino acid residue sequence corresponding to polypeptide formula p1, p2 or p3. An "antigenically related variant" is a polypeptide that immunoreacts with an antibody induced by a polypeptide according to formula p1, p2 or p3.

A subject polypeptide can be synthesized by any techniques that are known to those skilled in the polypeptide art. An excellent summary of the many techniques available may be found in J. M. Steward and J. D. Young, "Solid Phase Peptide Synthesis", W. H. Freeman Co., San Francisco, 1969, and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis.

C. Inocula

In another embodiment, a polypeptide of this invention, preferably a peptide corresponding to formula p1, p2, or p3 or an antigenically related variant thereof is used in a pharmaceutically acceptable aqueous diluent composition to form an inoculum that, when administered in an effective amount, is capable of inducing antibodies that immunoreact with an Integrin beta subunit to which the amino acid residue sequence of the polypeptide corresponds.

The word "inoculum" in its various grammatical forms is used herein to describe a composition containing a polypeptide of this invention as an active ingredient used for the preparation of antibodies against an Integrin beta subunit.

When a polypeptide is used to induce antibodies it is to be understood that the polypeptide can be used alone, or linked to a carrier as a conjugate, or as a polypeptide polymer, but for ease of expression the various embodiments of the polypeptides of this invention are collectively referred to herein by the term "polypeptide", and its various grammatical forms.

As already noted, one or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used. Exemplary additional linking procedures include the use of Michael addition reaction products, di-aldehydes such as glutaraldehyde, Klipstein et al., *J. Infect. Dis.*, 147, 318–326 (1983) and the like, or the use of carbodimide technology as in the use of a water-soluble carbodiimide to form amide links to the carrier. For a review of protein conjugation or coupling through activated functional groups, see Aurameas, et al., *Scand. J. Immunol., Vol.* 8, Suppl. 7:7–23 (1978).

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide or protein per unit dose depends, among other things, on the species of animal inoculated, the body weight of the animal and the chosen inoculation regimen as is well known in the art. Inocula typically contain polypeptide or protein concentrations of about 10 micrograms to about 500 milligrams per inoculation (dose), preferably about 50 micrograms to about 50 milligrams per dose.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent or vehicle such as water, saline or phosphate-buffered saline to form an aqueous composition. Such diluents are well known in the art and are discussed, for example, in *Remington's Pharmaceutical Sciences*, 16th Ed., Mack Publishing Company, Easton, Pa. (1980) at pages 1465–1467.

Inocula can also include an adjuvant as part of the diluent. Adjuvants such as complete Freund's adjuvant (CFA), incomplete Freund's adjuvant (IFA) and alum are materials well known in the art, and are available commercially from several sources.

D. Polyclonal and Monoclonal Anti-peptide Antibodies

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v).

An "antibody combining site" is that structural portion of an antibody molecule comprised of a heavy and light chain variable and hypervariable regions that specifically binds (immunoreacts with) antigen. The term "immunoreact" in its various forms means binding between an antigenic determinant-containing molecule and a molecule containing an antibody combining site such as a whole antibody molecule or a portion thereof.

"Antigenic determinant" refers to the actual structural portion of the antigen that immunologically bound by an antibody combining site. The terms is also used interchangeably with "epitope".

1. Polyclonal Antibodies

A polyclonal antibody of the present invention immunoreacts with a subject polypeptide, preferably a polypeptide corresponding in amino acid residue sequence to formula p1, p2 or p3. A subject polyclonal antibody is further characterized as not substantially immunoreacting with any Integrin alpha subunit or a polypeptide having an amino acid residue sequence identical to the 50 carboxy-terminal residues of the Integrin to which the amino acid residue sequence of the subject polypeptide corresponds.

A polyclonal antibody of the present invention is typically produced by immunizing a mammal with an inoculum of the present invention, preferably an inoculum containing a peptide corresponding to formula p1, p2 or p3, and thereby induce in the mammal antibody molecules having the appropriate polypeptide immunospecificity. The antibody molecules are then collected from the mammal and isolated to the extent desired by well known techniques such as, for example, by immunoaffinity chromatography. The polyclonal antibody so produced can be used in, inter alia, The diagnostic methods and systems of the present invention to discriminate between activated and nonactivated platelets or nucleated cells and in therapeutic methods for the purpose of modulating all adhesion.

2. Monoclonal Antibodies

A monoclonal antibody of the present invention is characterized as immunoreacting with an epitope formed by the RGD-binding region of an Integrin beta subunit that is homologous to residues 110-170 of GPIIIa. Preferably, a subject monoclonal antibody is further characterized as immunoreacting with a subject polypeptide, preferably a polypeptide corresponding to formula p1, p2 or p3.

The phrase "monoclonal antibody" in its various grammatical forms refers to a population of antibody molecules that contain only one species of antibody combining site capable of immunoreacting with a particular antigen. A monoclonal antibody composition thus typically displays a single binding affinity for any antigen with which it immunoreacts. A monoclonal antibody composition may therefore contain an antibody molecule having a plurality of antibody combining sites, each immunospecific for a different antigen, e.g., a bispecific monoclonal antibody.

A monoclonal antibody is typically composed of antibodies produced by clones of a single cell called a hybridoma that secretes (produces) but one kind of antibody molecule. The hybridoma cell is formed by fusing an antibody-producing cell and a myeloma or other self-perpetuating cell line. Such antibodies were first described by Kohler and Milstein, Nature 256:495-497 (1975), which description is incorporated by reference.

3. Methods

Monoclonal Antibody

The present invention contemplates a method of forming a monoclonal antibody that (a) immunoreacts with (a) a subject polypeptide, and (b) the Integrin beta subunit to which the amino acid residue sequence corresponds. The method comprises the steps of:

(a) Immunizing an animal with an Integrin beta subunit or a subject polypeptide. This is typically accomplished by administering an immunologically effective amount i.e., an amount sufficient to produce an immune response, of the immunogen to an immunologically competent mammal. Preferably, the mammal is a rodent such as a rabbit, rat or mouse. The mammal is then maintained for a time period sufficient for the mammal to produce cells secreting antibody molecules that immunoreact with the immunogen.

(b) A suspension of antibody-producing cells removed from the immunized mammal is then prepared. This is typically accomplished by removing the spleen of the mammal and mechanically separating the individual spleen cells is a physiologically tolerable medium using methods well known in the art.

(c) The suspended antibody producing cells are treated with a transforming agent capable of producing a transformed ("immortalized") cell line. Transforming agents and their use to produce immortalized cell lines are well known in the art and include DNA viruses such as Epstein Bar Virus (EBV), Simian Virus 40 (SV40), Polyoma Virus and the like, RNA viruses such as Moloney Murine Leukemia Virus (Mo-MuLV), Rous Sarcoma Virus and the like, myeloma cells such as P3X63-Ag8.653, Sp2/O-Ag14 and the like.

In preferred embodiments, treatment with the transforming agent results in the production of a hybridoma by fusing the suspended spleen cells with mouse myeloma cells from a suitable cell line by the use of a suitable fusion promoter. The preferred ratio is about 5 spleen cells per myeloma cell. A total volume of about $10^8$ splenocytes.

The cell line used should preferably be of the so-called "drug resistant" type, so that unfused myeloma cells will not survive in a selective medium, while hybrids will survive. The most common class is 8-azaguanine resistant cell lines, which lack the enzyme hypoxanthine guanine phophoribosyl transferase and hence will not be supported by HAT (hypoxanthine, aminopterin, and thymidine) medium. It is also generally preferred that the myeloma cell line used be of the so-called "non-secreting" type, in that it does not itself produce any antibody, although secreting types may be used. In certain cases, however, secreting myeloma lines may be preferred. While the preferred fusion promoter is polyethylene glycol having an average molecule weight from about 1000 to about 4000 (commercially available as PEG 1000, etc.), other fusion promoters known in the art maybe employed.

(d) The transformed cells are then cloned, preferably to monoclonality. The cloning is preferably performed in a tissue culture medium that will not support nontransformed cells. When the transformed cells are hybridomas, this is typically performed by diluting and culturing in separate containers, the mixture of unfused spleen cells, unfused myeloma cells, and fused cells (hybridomas) in a selective medium which will not support the unfused myeloma cells for a time sufficient to allow death of the unfused cells (about one week). The dilution may be a type of limiting one, in which the volume of diluent is statistically calculated to isolate a certain number of cells (e.g., 1-4) in each separate container (e.g., each well of a microtiter plate). The medium is one (e.g., HAT medium) which will not support the drug-resistant (e.g., 8-azaguanine resistant) unfused myeloma cell line.

(e) The tissue culture medium of the cloned transformants is evaluated for the presence of secreted antibody molecules that immunoreact with the immunogen and its corresponding subject polypeptide or Integrin beta subunit.

(f) Once a desired transformant has been identified in step (e), it is selected and grown in a suitable tissue culture medium for a suitable length of time, followed by recovery of the desired antibody from the culture supernatant. The suitable medium and suitable length of culturing time are known or are readily determined.

To produce a much greater concentration of slightly less pure monoclonal antibody, the desired hybridoma may be injected into mice, preferably syngenic or semi-syngenic mice. The hybridoma will cause formation of antibody-producing tumors after a suitable incubation time, which will result in a high concentration of the desired antibody (about 5-20 mg/ml) in the bloodstream and peritoneal exudate (ascites) of the host mouse.

Media useful for the preparation of these compositions are both well known in the art and commercially available and include synthetic culture media, inbred mice and the like. An exemplary synthetic medium is Dulbecco's minimal essential medium [DMEM; Dulbecco et al., *Virol.* 8:396 (1959)] supplemented with 4.5 gm/$^1$ glucose, 20 mm glutamine, and 20% fetal calf serum. An exemplary inbred mouse strain is the Balb/c.

A monoclonal antibody produced by the above method can be used, for example, in diagnostic and therapeutic modalities wherein formation of an Integrin beta subunit immunoreaction product is desired. Exemplary reaction products include a GPIIIa-containing immunoreaction product.

E. Hybridomas and Methods of Preparation

Hybridomas of the present invention are those which are characterized as having the capacity to produce a subject monoclonal antibody.

A preferred hybridoma of the present invention is characterized as producing antibody molecules that also immunoreact with a cytoadhesion, preferably GPIIIa.

Methods for producing hybridomas producing (secreting) antibody molecules having a desired immunospecificity, i.e., having the ability to immunoreact with a particular protein, an identifiable epitope on a particular protein and/or a polypeptide, are well known in the art. Particularly applicable is the hybridoma technology described by Niman et al., *Proc. Natl. Acad. Sci. U.S.A.*, 80:4949-4953 (1983), and by Galfre et al., *Meth. Enzymol.*, 73:3-46 (1981), which descriptions are incorporated herein by reference.

F. Therapeutic Methods and Compositions

A subject polypeptide can be used to modulate the adhesion in vivo of cells expressing the Integrin beta subunit to which the polypeptide corresponds.

For instance, a subject polypeptide corresponding to formula p1 can be used in a pharmaceutically acceptable composition that, when administered to a human subject in an effective amount, is capable of competitively inhibiting the aggregation of platelets. That inhibition is believed to result in a decreased rate of thrombus formation. Thus, in vivo administration of a subject polypeptide can be used to modulate any physiological response initiated by adhesion such as coagulation and some inflammatory responses.

In another embodiment, the aggregation of platelets can be inhibited by intravenous administration of an effective amount of a pharmaceutically acceptable composition comprising a subject polyclonal antibody that immunoreacts with a polypeptide according to formula p1.

A preferred method of modulating platelet adhesion contemplates administering a platelet aggregation-inhibiting amount of a subject monoclonal antibody that immunoreacts with the RGD-binding region (residues 110-170) of GPIIIa. More preferably, the monoclonal antibody used in a plate et-inhibiting therapeutic method is further characterized as immunoreacting with a polypeptide corresponding to formula p1.

The polypeptide- or antibody molecule-containing compositions administered take the form of solutions or suspensions, however, polypeptides can also take the form of tablets, pills, capsules, sustained release formulations or powders. In any case, the polypeptide-containing compositions typically contain about 0.1 uM to about 1.0 M of polypeptide as active ingredient, preferably about 1.0 uM to about 10 millimolar (mM), whereas the antibody molecule-containing compositions typically contain about 10 ug/ml to about 20 mg/ml of antibody as active ingredient, preferably about 1 mg/ml to about 10 mg/ml.

The preparation of a therapeutic composition that contains polypeptides or antibody molecules as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient as are well known. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide or antibody can be formulated into the therapeutic composition as neutralized pharmaceutically acceptable salt forms. Pharmaceutically acceptable salts include the acid addition salts (formed with the free amino groups of the polypeptide or antibody molecule) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide- or antibody containing compositions are conventionally administered intravenously, as by injection of a unit dose, for example. The term "unit dose" when used in reference to a therapeutic composition of the present invention refers to physically discrete units suitable as unitary dosages for humans, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject to utilize the active ingredient, and degree of inhibition of receptor-ligand binding desired. Precise amounts of active ingredient required to be administered depend on the judgment of the practitioner and are peculiar to each individual. However, suitable dosage ranges are of the order of one to several milligrams of active ingredient per individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain therapeutically effective concentrations in the blood are contemplated. For a subject polypeptide, therapeutically effective blood concentrations are in the range of about 0.1 mM to about 10 mM, preferably about 1.0 mM. Therapeutically effective blood concentrations of antibody molecules of the present invention are in the range of about 0.1 uM to about 10 uM, preferably 1.0 uM.

G. Diagnostic Systems

A diagnostic system in kit form of the present invention includes, in an amount sufficient for at least one assay, an expressed polypeptide, polyclonal antibody or monoclonal antibody of the present invention, as a separately packaged reagent. Instructions for use of the packaged reagent are also typically included.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In one embodiment, a diagnostic system for assaying for activated platelets in a platelet-containing vascular fluid sample, such as blood or plasma, comprises a package containing a subject polyclonal antibody that immunoreacts with a polypeptide corresponding to formula p1. In another embodiment, a diagnostic system for assaying for activated platelets in a platelet-containing vascular fluid sample comprises a package containing a subject monoclonal antibody that immunoreacts with an epitope formed by the RGD-binding region (residues 110-170) of GPIIIa, and preferably also immunoreacts with a polypeptide corresponding to formula p1. Further preferred are kits wherein the antibody molecules of the polyclonal or monoclonal antibody are linked to a label.

Thus, in preferred embodiments, a diagnostic system of the present invention further includes a label or indicating means capable of signaling the formation of a complex containing the antibody molecules of a polyclonal or monoclonal antibody of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. "In vivo" labels or indicating means are those useful within the body of a human subject and include $^{111}$In, $^{99}$Tc, $^{67}$Ga, $^{186}$Re, and $^{132}$I. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel protein methods and/or systems.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol. Vol. 8 Suppl. 7:7-23 (1978), RodWell et al., Biotech. 3:889-894 (1984), and U.S. Pat. No. 4,493,795.

The diagnostic systems can also include, preferably as a separate package, a specific binding agent. A "specific binding agent" is a molecular entity capable of selectively binding a reagent species of the present invention but is not itself a protein expression product, polypeptide, or antibody molecule of the present invention. Exemplary specific binding agents are antibody molecules, complement proteins or fragments thereof, protein A and the like. Preferably, the specific binding agent can bind the antibody molecule or polypeptide of this invention when it is present as part of a complex.

In preferred embodiments the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the presence or quantity of fibrinogen-bound platelets in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of *Basic and Clinical Immunology* by D. P. Sites et al., published by Lange Medical Publications of Los Altos, Cal. in 1982 and in U.S. Pat. No(s). 3,654,090; 3,850,752; and 4,016,043, which are all incorporated herein by reference.

Thus, in preferred embodiments, the expressed protein, polypeptide, or antibody molecule of the present invention can be affixed to a solid matrix to form a solid support that is separately packaged in the subject diagnostic systems.

The reagent is typically affixed to the solid matrix by adsorption from an aqueous medium although other modes of affixation, well known to those skilled in the art can be used.

Useful solid matrices are well known in the art. Such materials include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packages discussed herein in relation to diagnostic systems are those customarily utilized in diagnostic systems. Such packages include glass and plastic (e.g., polyethylene, polypropylene and polycarbonate) bottles, vials, plastic and plastic-foil laminated envelopes and the like.

H. Assay Methods

The present invention contemplates any method that results in detecting an Integrin beta subunit, and particularly GPIIIa, by producing a complex containing an antibody molecule contained in a polyclonal antibody or monoclonal antibody of the present invention. Those skilled in the art will understand that there are numerous well known clinical diagnostic chemistry procedures that can be utilized to form those complexes. Thus, while exemplary assay methods are described herein, the invention is not so limited.

For example, a heparin-preserved (non-clotted) blood sample and $^{125}$I-labeled antibody molecules are admixed. The immunoreaction admixture thus formed is maintained under immunological assay conditions for a time period sufficient for any activated platelets to immunoreact with the labeled antibodies and form a labeled immunoreaction product. The labeled immunoreaction products are then separated from the non-reacted labeled-antibodies, typically by centrifugation sufficient to pellet all platelets present in the sample. The amount of labeled immunoreaction product formed is then assayed.

Immunological assay conditions are those that maintain the immunological activity of the antibody molecules contained in a polyclonal or monoclonal antibody of this invention and the Integrin molecules sought to be assayed. Those conditions include a temperature range of about 4 degrees C. to about 45 degrees C., preferably about 37 degrees C., a pH value range of about 5 to about 9, preferably about 7 and an ionic strength varying from that of distilled water to that of about one molar sodium chloride, preferably about that of physiological saline. Methods for optimizing such conditions are well known in the art.

I. DNA Segments

In living organisms, the amino acid residue sequence of a protein or polypeptide is directly related via the genetic code to the deoxyribonucleic acid (DNA) sequence of the structural gene that codes for the protein. Thus, a structural gene can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences can code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A DNA segment of the present invention includes a structural gene that encodes a polypeptide containing an Integrin beta subunit amino acid residue sequence homologous to the GPIIIb sequence located between residues 110-170 as shown in FIG. 1.

A preferred DNA segment of the present invention includes a DNA sequence that codes for an amino acid residue sequence corresponding to, and preferably identical to, a sequence represented by polypeptide formula p1, p2 or p3. Preferably, the DNA sequence is present as an uninterrupted linear series of codons where each codon codes for an amino acid residue found in the above described amino acid residue sequences, i.e., a DNA sequence containing no introns.

Thus, a DNA segment consisting essentially of the nucleotide sequence shown in FIG. 1 from about base 123 to about base 611 constitutes one embodiment of the present invention.

A DNA segment of the present invention can easily be synthesized by chemical techniques, for example, the phosphotriester method of Matteucci et al., *J. Am. Chem. Soc.*, 103:3185 (1981). Of course, by chemically synthesizing the coding sequence, any desired modifications can be made simply by substituting the appropriate bases for those encoding the native amino acid residue sequence. However, DNA molecules including sequences exactly homologous to those shown in FIG. 1 are preferred.

The DNA molecules of the present invention typically have cohesive termini, i.e., "overhanging" single-stranded portions that extend beyond the double-stranded portion of the molecule. The presence of cohesive termini on the DNA molecules of the present invention is preferred.

Also contemplated by the present invention are ribonucleic acid (RNA) equivalents of the above described DNA segments.

J. Recombinant DNA Molecules

A recombinant DNA molecule of the present invention can be produced by operatively linking a vector to a DNA segment of the present invention, preferably a DNA segment coding for a polypeptide corresponding to formula p1, p2 or p3.

As used herein, the term "vector" refers to a DNA molecule capable of autonomous replication in a cell and to which another DNA segment can be operatively linked so as to bring about replication of the attached segment. Vectors capable of directing the expression of genes encoding proteins having GPIIIa-related amino acid residue sequences are referred to herein as "expression vectors". Thus, a recombinant DNA molecule (rDNA) is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the gene encoding a polypeptide having an Integrin beta subunit-related amino acid residue sequence included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the gene encoding a GPIIb-related amino acid residue sequence in a bacterial host cell, such as E. coli, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Bio-Rad Laboratories, (Richmond, Cal.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), and pTDT1 (ATCC, #31255).

In preferred embodiments, the eucaryotic cell expression vectors used to construct the recombinant DNA molecules of the present invention include a selection marker that is effective in a eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.* 1:327–341 (1982).

The use of retroviral expression vectors to form the rDNAs of the present invention is also contemplated. As used herein, the term "retroviral expression vector" refers to a DNA molecule that includes a promoter sequence derived from the long terminal repeat (LTR) region of a retrovirus genome.

In preferred embodiments, the expression vector is typically a retroviral expression vector that is preferably replication-incompetent in eucaryotic cells. The construction and use of retroviral vectors has been described by Sorge et al., *Mol. Cell. Biol.* 4:1730–37 (1984).

A variety of methods have been developed to operatively link DNA to vectors via complementary cohesive termini. For instance, complementary homopolymer tracts can be added to the DNA segment to be inserted and to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. A DNA segment having cohesive termini is treated with bacteriophage T4 DNA polymerase or E. coli DNA polymerase I, enzymes that remove protruding, 3', single-stranded termini with their 3'-5' exonucleolytic activities and fill in recessed 3' ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies, Inc., New Haven, Conn.

Also contemplated by the present invention are RNA equivalents of the above described recombinant DNA molecules.

K. Transformed Cells and Cultures

The present invention also relates to a host cell transformed with a recombinant DNA molecule of the present invention. The host cell can be either procaryotic or eucaryotic. Bacterial cells are preferred procaryotic host cells and typically are a strain of E. coli such as, for example the E. coli strain DH5 available from Bethesda Research Laboratories, Inc., Bethesda, Md. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658.

Transformation of appropriate host cells with a recombinant DNA molecule of the present invention is accomplished by well known methods that typically depend on the type of vector used. With regard to transformation of procaryotic host cells, see, for example, Cohen et al., *Proc. Natl. Acad. Sci. U.S.A.*, 69:2110 (1972); and Maniatis et al., *Molecular Cloning, A Laboratory Mammal.* Cold Spring Harbor Laboratory, Cold Spring Harbor, N.Y. (1982). With regard to transformation of vertebrate cells with retroviral vectors containing rDNAs, see, for example, Sorge et al., *Mol. Cell. Biol.* 4:1730-37 (1984); Graham et al., *Virol.*, 2:456 (1973); and Wigler et al., *Proc. Natl. Acad. Sci. U.S.A.*, 76:1373-76 (1979).

Successfully transformed cells, i.e., cells that contain a recombinant DNA molecule of the present invention, can be identified by well known techniques. For example, cells resulting from the introduction of an rDNA of the present invention can be cloned to produce monoclonal colonies. Cells from those colonies can be harvested, lysed and their DNA content examined for the presence of the rDNA using a method such as that described by Southern, *J. Mol. Biol.* 98:503 (1975) or Berent et al., Biotech., 3:208 (1985).

In addition to directly assaying for the presence of rDNA, successful transformation can be confirmed by well known immunological methods when the rDNA is capable of directing the expression of a subject polypeptide. For example, cells successfully transformed with a subject rDNA containing an expression vector produce a polypeptide displaying a characteristic antigenicity. Samples of a culture containing cells suspected of being transformed are harvested and assayed for a subject polypeptide using antibodies specific for that polypeptide antigen, such as those produced by a hybridoma of the present invention.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains a protein displaying Integrin beta subunit antigenicity.

Nutrient media useful for culturing transformed host cells are well known in the art and can be obtained from several commercial sources. In embodiments wherein the host cell is mammalian, a "serum-free" medium is preferably used.

L. Methods for Producing A Subject Polypeptide

Another aspect of the present invention pertains to a method for producing a subject polypeptide useful for raising antibodies which can be used in the diagnostic systems and methods of the present invention.

The present method entails initiating a culture comprising a nutrient medium containing host cells transformed with a recombinant DNA molecule of the present invention that is capable of expressing a gene encoding a subject polypeptide, preferably a polypeptide corresponding to formula p1, p2 or p3. The culture is maintained for a time period sufficient for the transformed cells to express the subject polypeptide. The expressed polypeptide is then recovered from the culture.

Methods for recovering an expressed polypeptide from a culture are well known in the art and include fractionation of the polypeptide-containing portion of the culture using well known biochemical techniques. For instance, the methods of gel filtration, gel chromatography, ultrafiltration, electrophoresis, ion exchange, affinity chromatography and the like, such as are known for protein fractionations, can be used to isolate the expressed proteins found in the culture. In addition, immunochemical methods, such as immunoaffinity, immunoabsorption and the like can be performed using well known methods.

EXAMPLES

The following examples are intended to illustrate, but not limit, the present invention.

1. Identification of an Adhesion Protein Binding Site on an Integrin

Chemical crosslinking has been used extensively to study the interactions of RGD-containing ligands with GPIIb-IIIa. Bennett et al., *J. Biol. Chem.* 257:8049 (1982). Most recently, crosslinking approaches have been used to examine the interaction of small RGD peptides of six to fourteen amino acids with GPIIb-IIIa as a means of characterizing the topography of the RGD recognition site. Santero et al., *Cell.* 48:867 (1987) and D'Souza et al., *J. Biol. Chem.*, 263:3943 (1988). These studies have shown that platelet activation with agonist, an event necessary for binding of adhesive proteins such as fibrinogen and fibronectin to GPIIb-IIIa, markedly and selectively enhances the crosslinking of the RGD-peptides to GPIIIa, the beta subunit of the lutegin GPIIb-IIIa.

The present study defines a discrete site within GPIIIa to which a small RGD-peptide can be chemically crosslinked. The amino acid residue sequence of this region is conserved in other members of the Integrin family indicating it plays a critical role in the function of this family of adhesion receptors.

A. RGD-Peptide Preparation

The RGD-peptide used in this study, designated Fn-7, has the amino acid residue sequence KYGRRGDS. This peptide was designed to contain a lysine residue (K) to facilitate crosslinking and a tyrosine residue (Y) to provide a site for radioiodination. Fn-7 was prepared by solid-phase synthesis on an Applied Biosystems model 430 peptide synthesizer using peptidylglycine a-amidating monooxygenase resins and t-Boc amino acids purchased from Applied Biosystems. The peptide was analyzed for homogeneity by high performance liquid chromatography using a C18μ Bondapak column with a linear gradient of 0-60% acetonitrile in 0.1% trifluoroacetic acid and was found to be >85% homogeneous. The amino acid composition of the peptide was determined after about a 24 hour period, the hydrolysates being in a6 N HCl, and the results were consistent with theoretical yields. Peptides were dissolved in phosphate buffered saline (PBS) prior to use and the pH was adjusted to 7.2.

Fn-7 was radioiodinated by a modified lactoperoxidase-glucose oxidase method see Lam et al., *J. Biol. Chem.* 262:947-950 (1987). Briefly glucose (20 μg in 40 μl of 0.2 M sodium phosphate, pH 7.4), carrier-free $Na^{125}I$ and the other reagents by gel filtration on a Bio-Gel P-2 column. The conditions for radioiodination were selected to minimize ligand heterogeneity, and >80% of the iodinated peptide was in the monoiodotyrosinated form using this protocol. The concentration of the labeled peptide was determined by absorbance at 280 nm, using extinction coefficients derived from the amino acid compositions. The specific activity of the peptide was 5-8 mCi/mg.

B. Platelet Preparation and Chemical Crosslinking of Peptide Fn-7 to Discrete Sites on GPIIIa Platelets were isolated from fresh human blood collected into acid/citrate/dextrose by differential centrifugation followed by gel filtration on Sepharose 2B in divalent ion-free Tyrode's buffer, pH 7.3, containing 0.1% bovine serum albumin. See, Marguerie et al., *J. Biol. Chem.* 225:154-161 (1980).

Platelet binding of Fn-7 followed the protocols previously described for measuring platelet interactions with adhesive proteins and with this and other peptides. See, Ginsberg et al., *J. Biol. Chem.* 260:3931-3936 (1985); Lam et al., *Fed. Proc. Fed. Am. Soc. Exp. Biol.*, 44:1126 (1985); and Marguerie et al., suora. Briefly, platelets were suspended at $4 \times 10^8$/ml in divalent ion-free Tyrode's albumin buffer. Unless otherwise specified, $Ca^{2+}$ was added to a final concentration of 1 mM. The platelet stimulus used was 0.5 unit/ml —thrombin. The radiolabeled peptide was then added to $6 \times 10^8$ cells/ml stimulated or nonstimulated platelets at a concentration of 20 µM, and binding proceeded for 45 min at 22° C. The selected cross-linking agent was then added. The cross-linking agent used in this study, bis(sulfosuccinimidyl) suberate (BS), purchased from Pierce Chemical Co. was dissolved in PBS immediately prior to use and admixed with the platelets to a final concentration of 0.2 mM. The cross-linking reactions were terminated after 10 min at 22° C. by addition of 10 mM Tris, pH 7.0.

The cell-bound ligand was recovered by centrifugation through 20% sucrose, and the cells were extracted in PBS containing 1% Nonidet P40 and 10 mM N-ethylmaleimide (Sigma). Extracted proteins were precipitated with 10% trichloroacetic acid, and the pellet obtained after centrifugation was washed three times with cold 85% ethanol. The cross-linked samples were analyzed by electrophoresis (SDS-PAGE) on polyacrylamide vertical slab gels in the buffer system of Laemmli, *Nature*, 227 680-635 (1970). For disulfide bond reduction, the samples were treated with 5% 2-mercaptoethanol. Gels were dried and autoradiograms were developed with Kodak X-Omat AR films. Molecular weights were estimated on the basis of electrophoretic mobility relative to standards obtained either from Sigma Chemical or from Bethesda Research Laboratories.

C. Immunoblotting Procedures

Cross-linked samples were immunoprecipitated using a monoclonal antibody designated 22C4, which recognizes GPIIIa, Ginsberg et al., *J. Biol. Chem.*, 262:5437 (1987). Washed acid-precipitates, obtained from the cross-linked samples as described above, were dissolved in 250 ml of immunoprecipitation buffer (IPB) which contained 0.15 M NaCl, 0.01 M EDTA, 10 mM benzamidine-HCl, soybean trypsin inhibitor (10 µg/ml), 0.2 mM phenylmethanesulfonyl fluoride, 1% (v/v) Triton X-100, 0.05% Tween 20, 0.02% $NaN_3$, and Trasylol (5 units/ml) in 0.02 M Tris-HCl, Ph 7.4. The IPB has been found to dissociate the complex of GPIIb-IIIa. The samples were precleared by adding 15 ml of heat-inactivated normal rabbit serum followed by protein A reagent (Pansorbin, Behring Diagnostics). The cleared lysates were then supplemented with 1% bovine serum albumin and 150 ml of IPB containing 10 ml of the above monoclonal antibody. Samples were incubated overnight at 4° C., and Pansorbin was then added. After 1 h at 22° C., samples were centrifuged, and the recovered immunoprecipitates were washed three times by centrifugation in IPB. The precipitates were solubilized by heat for 3 min at 100° C. in Laemmli sample buffer and then subjected to SDS-PAGE as described above. For immunoblotting, protein samples were resolved on SDS-PAGE as indicated above. After electrophoresis, the resolved proteins were transferred onto polyvinylidene difluoride membranes (PVDF). The transfers were probed with the anti-GPIIIa monoclonal antibody, 22C4 an anti-GPIIIa polyclonal antibody or with a rabbit antiserum raised to a peptide having a sequence corresponding to residues 636-654 of GPIIIa. The bound antibodies were detected using anti-mouse IgG conjugated to horseradish peroxidase (Bio-Rad) and 4-chloro-1-napthol as substrate.

D. Chymotryptic Fragmentation of GPIIIa

Chymotryptic cleavage of platelets degrades the 100 kDa GPIIIa subunit to release approximately one-third of the molecule from the cell and to form a core comprised of a 66 kDa degradation product which can then be further degraded to 55-66 kDa fragments that remain cell-associated. Kornecki et al., *J. Biol. Chem.*, 258:8349 (1983), McGowan et al., *J. Biol. Chem.*, 258:11243 (1983) and McGregor et al., *Eur. J. Biochem.*, 148:97 (1985).

Initial studies were performed to determine if Fn-7 crosslinked to GPIIIa with $BS^3$ was retained or released from the cell by chymotrypsin. $^{125}$I-Fn-7 was crosslinked to thrombin-stimulated platelets as described herein before in Example 1B. Crosslinked cells were then admixed with chymotrypsin (0.5 mg/ml final concentration) and maintained for 4 hours at 22° C. The radioactivity released from the cells was quantitated.

In each of four chymotryptic digests, 50-70% of the cell-associated °I-Fn-7 was released from the platelets by chymotrypsin treatment. When the supernatant from the digested platelets was treated with 10% trichloroacetic acid, only 6-8% of the radioactivity was precipitated, indicating that Fn-7 was released in association with small peptides. When the supernatant or its acid precipitate was analyzed by SDS-PAGE on 15% acrylamide gels, the radioactivity migrated more rapidly than an 8 kDa molecular weight standard.

The cell-associated radioactivity after chymotrypsin treatment was recovered by centrifugation and analyzed by SDS-PAGE as described hereinbefore. As shown in FIG. 2 (lane 2), the only radioactive band detected from the digested platelets was residual, intake GPIIIa. Chymotrypsin diminished the Fn-7 radioactivity associated with GPIIIa but did not generate discrete radioactive degradation products, particularly at the 66 kDa position.

Immunoblotting (FIG. 3) of the same digest with either a polyclonal antiserum to GPIIb-IIIa (lane 4) or a monoclonal antibody to GPIIIa (lane 6) demonstrated that the enzyme had generated major derivatives at 66 and 55 kDa. As neither of these bands were radioactive, the Fn-7 crosslinking site does not reside in the 66 kDa domain of GPIIIa and is released from the cell by chymotryptic cleavage.

As the putative membrane spanning domain of GPIIIa lies close to its COOH-terminus, the 66 kDa fragments immunoblotted with an antipeptide antibody raised to an amino acid sequence of GPIIIa (residues 636–654), proximal to the putative membrane spanning region (beginning at residue 693). Therefore, the Fn-7 crosslinking site is not present in the 66 kDa COOH-terminal region of the GPIIIa and resides in the 34 kDa NH$_2$-terminal region of the subunit as diagramically shown in FIG. 4 (steps 1 and 2).

As previously shown in FIG. 2, chymotryptic cleavage of isolated GPIIIa yields two Fn-7 labeled fragments. To determine the origin of these fragments from within GPIIIa, their NH$_2$-terminal amino acid residue sequences were identified. To this end, preparative crosslinking of $^{125}$I-Fn-7 to thrombin-stimulated platelets was undertaken; and, ultimately, the GPIIIa:Fn-7 complex from 6 units of blood was isolated by SDS-PAGE followed by elution. The isolated product was digested with chymotrypsin and subjected to HPLC reverse phase chromatography on a C18 column. The radioactivity was pooled into two fractions enriched in either the 23 or the 14 kDa fragments, each of which was subjected to SDS-PAGE on a 15% gel under reducing conditions, and transferred to polyvinylidene difluoride (PVDF) membranes.

Autoradiograms of the transfers containing the $^{125}$I-Fn-7 labeled GPIIIa fragments are shown in FIG. 4 (Step 3), and both the 23 and 14 kDa fragments are apparent. The bands were cut from the transfers and subjected to NH-terminal sequence analysis using standard automated amino acid residue sequencing technology.

A single predominant sequence was obtained for the 23 kDa fragment (FIG. 4). The residues identified at the first four positions accounted for 72 to 87% of the total yield at these positions. At all of the determined positions for the nine cycles performed, the amino acids were identical to the NH$_2$-terminal sequence of GPIIIa. This places the Fn-7 crosslinking site within the 23 kDa NH$_2$-terminal region of GPIIIa.

In the 14 kDa fragment, a major sequence predominated for 22 cycles and coincided to residues 91–112 of GPIIIa. (A second sequence was detected at a lower yield but was identical to an internal sequence with chymotrypsin). The residue at position 90 of GPIIIa is leucine, a preferred chymotrypsin cleavage site. At 14 kDa, the smaller GPIIIa fragment is predicted to extend to residues 200–220 of the glycoprotein, and a 23 kDa fragment extending from the NH$_2$-terminus should also terminate within the same region of GPIIIa. Thus, these positionings of the Fn-7 crosslinking site are consistent with one another and with the localization to the NH$_2$-terminal 34 kDa region released from intact platelets by chymotrypsin.

E. V8 Protease Fragmentation of GPIIIa.

A similar approach was taken to characterize the V8 protease fragments of GPIIIa containing the Fn-7 crosslinking site. After the steps of enzymatic digestion of GPIIIa:Fn-7 complex, HP: chromatography, SDS-PAGE and transfer, the 8 and 10 kDa doublet was observed on the autoradiogram of the transfer (FIG. 4, Step 4). These bands were excised from the transfer and sequenced separately. The 10 kDa fragment yielded a single NH$_2$-terminal sequence that extended for 16 residues. This sequence corresponded precisely to that predicted for residues 109–124 of GpIIIa. The amino acid residue at position 108 of GPIIIa is glutamic acid, a preferred cleavage site for V8 protease. Interestingly, although a strong signal was obtained for the methionine at position 124, no signal was obtained at the next residue, predicted to be a lysine. Thus, the lysine at the 125 position is a candidate for direct crosslinking to the lysine in Fn-7.

The 10 kDa fragment extending from residue 109 is predicted to terminate in the vicinity of residue 200. The sequence signal of the 8 kDa fragment was not as strong as that of the 10 kDa derivative, but the first four positions were clear and were identical to those of the 10 kDa fragment. With the same NH$_2$-terminus at residue 109 but being 2 kDa smaller, the 8 kDa fragment should terminate in the 170–180 region; two glutamic acids occur within this 10 amino acid stretch. It is noteworthy that the NH$_2$-terminal sequence of the 8 and 10 kDa fragments was also detected within the sequence determined for the 14 kDa chymotryptic fragment, providing independent confirmation of the localization of the Fn-7 crosslinking site.

F. Localization of the RGD-Binding Site

The above observations indicate that the Fn-7 crosslinking site resides in the NH$_2$-terminal region of GPIIIa. Affinity chromatography experiments were undertaken to determine if the RGD binding site also resided in this region. Previous studies have documented that GPIIb-IIIa can be selectively bound to RGD affinity columns from detergent extracts of platelets and specifically eluted by free RGD peptide. Pytela et al., *Science*. 231:1559 (1986).

Platelets were either untreated or digested with chymotrypsin. The chymotrypsin conditions were chosen such that approximately 50% of the GPIIIa was degraded to the 66 kDa derivative.

The two platelet preparations were then solubilized with octylglucoside, and the extracts were passed over an RGD affinity column. After washing to obtain a passed-through fraction, the column was eluted with free RGD peptide. The pass-through and the eluate were subjected to SDS-PAGE on 7% gels under non-reducing conditions, transferred, and immunoblotted with anti-GPIIIa monoclonal antibody 22C4.

As shown in FIG. 5, intact GPIIIa was observed in the pass-through from the undigested platelets and mixture of intact GPIIIa and the 66 kDa GPIIIa fragment were present in the pass-through from the chymotrypsin-treated platelets. In the RGD eluates from both columns, only intake GPIIIa was detected. Thus, the 66 kDa fragment was not retained on the RGD affinity column. This result is compatible with the interpretation that the site which RGD peptides bind, and to which they crosslink, coincide and reside in the NH$_2$-terminal aspects of GPIIIa. This conclusion is also consistent with a report of the inhibition of platelet aggregation by a monoclonal antibody to the NH$_2$-terminal region of GPIIIa. Calvete et al., *Biochem. J.* 250:697 (1988).

G. Relationship of the RGD Crosslinking Site in GPIIIa to Other Integrins

GPIIIa is a protein 762 amino acid residues in length. Fitzgerald et al., *J. Biol. Chem.* 262:3926 (1987). Based upon the amino acid residue sequences of the chymotryptic and V8 protease fragments, the RGD crosslinking site has been confined to a region, of about 63 amino acids (the first glutamic acid residue in the GPIIIa 170-180 region), extending COOH-terminal from residue 109. In view of the broad utilization of the RGD recognition specificity throughout the Integrin family, a comparison of the primary structure of this region among the three beta subunits of the human Integrins is of considerable interest.

An alignment of the amino acid residue sequences of this region of the beta subunits of the LeuCam, the VLA and the Cytoadhesin subfamilies is shown in FIG. 6. In addition, the deduced sequences of the beta subunits of avian and Xenopus Integrins are included. The amino acid sequence with in this region of the Integrins is remarkably conserved, not only in the human proteins but also in the avian and amphibian proteins. In the consensus sequence, requiring an amino acid identity at each position in at least four of the five proteins, 47 of the 63 residues (75%) are specified. GPIIIa fits this consensus sequence at 38 of the 63 residues. The conserved nature of this region of the Integrins greatly exceeds the overall identity among Integrins. Such conservation is clearly compatible with a contribution of this region to the function of these Integrins as adhesion receptors.

As noted, members of each of the three families of human Integrins [Pytela et al., *Science*. 231:1559 (1986), Ruoslahti et al., *Cell.* 44:517 (1986), Pytela et al., *J. Cell Biol.* 102:442 (1986) and Wright et al., *Proc. Natl. Acad. Sci. U.S.A.* 84 (1987)] and the avian Integrin [Horwitz et al., *J. Cell Biol.*, 103:2421 (1986)] can bind ligands via an RGD recognition specificity. The localization of the RGD crosslinking site in GPIIIa to this region is the first direct implication of the region in Integrin function. Within this 63 amino acid stretch of GPIIIa, there are four lysine residues that could be directly involved in the crosslinking reaction; and, based on the amino acid sequence analysis of the 10 kDa V8 protease fragment, the lysine at position 125 is a prime candidate for this function.

The members of the LeuCam family apparently exhibit the lowest affinity of the three human Integrin families for RGD peptides and can bind ligands that lack RGD sequences [(I-CAM, a ligand for LFA-1, lacks an RGD sequence Horwitz et al., *J. Cell Biol.*, 103:2421 (1986)]. The LeuCam beta chain is the only one of the five determined beta chain sequences that does not have a lysine at the position corresponding to residue 125 of GPIIIa; a non-conservative leucine substitution occurs for the lysine. It is also noted in comparing the sequence of GPIIIa to the other Integrins that a non-conserved region, GPIIIa residues 129-149, is flanked by two very highly conserved regions. This non-conserved region is a clear candidate for imparting functions to GPIIb-IIIa, such as its high affinity for multiple RGD ligands, that distinguish it from the other Integrins.

Furthermore, it should be noted that the RGD crosslinking site on GPIIIa certainly need not constitute the complete recognition site(s) involved in the binding of adhesive proteins such as fibrinogen to GPIIb-IIIa or other Integrins. Indeed, it has been suggested that fibrinogen may bind to additional regions of GPIIb-IIIa [Kornecki et al., *J. Biol. Chem.*, 258:8349 (1983), Parise et al., *Blood, Suppl.* 70:357a (1987)] via non-RGD sequences, namely the extreme COOH-terminal aspects of the gamma chain of fibrinogen Kloczewiak et al., *Biochemistry*, 23:1767 (1984). Although gamma chain peptides can inhibit the binding and crosslinking of RGD peptides to GPIIIa [Santoro et al., *Cell.* 48:867 (1987)] have shown that these peptides become crosslinked to GPIIb. The present studies have confirmed these results.

The foregoing specification, including the specific embodiments need examples, is intended to be illustrative of the present invention and is not to be taken as limiting. Numerous other variations and modifications can be effected without departing from the true spirit and scope of the present invention.

What is claimed is:

1. A polypeptide of 60 to 90 amino acid residues in length having a sequence homologous to the GPIIIa amino acid residue sequence represented by the formula: DYPVDIYYLMDLSYSMKDDLWSIQNLGTKLATQMRKLTSNLRIGFGAFVDKPVSPYMYISPPE.

2. A polypeptide corresponding in amino acid residue sequence to the formula:
   a) DYPVIDYYLMDLSYSMKDDLWSIQNLGTKLATQMRKLTSNLRIGFGAFVDKPVSPYMYISPPE,
   b) GYPIDLYYLMDLSYSMLDDLRNVKKLGGDLLRALNEITESGRIGFGSFVDKTVLPFVNTHP, or
   c) DYPIDLYYLMDLSYSMKDDLENVKSLGTDLMNEMRRITSDFRIGFGSFVEKTVMPYISTTP.

3. A recombinant DNA molecule comprising a vector operatively linked to a DNA segment that defines a structural gene coding for a polypeptide according to claim 1, wherein said structural gene contains no more than 2,000 base pairs.

4. The recominant DNA molecule of claim 5 wherein said structural gene codes for a polypeptide according to claim 2.

5. The recombinant DNA molecule of claim 3 wherein said vector is capable of expressing said structural gene in a host cell.

6. The recombinant DNA molecule of claim 3 wherein said structural gene has a nucleotide base sequence represented by the formula:
GATTACCCTGTGGACATCTACTACTTGATGGACCTGTCTTACTCCATGAAGGATGATCTGTGGA GCATCCAGAACCTGGGTACCAAGCTGGCCACCCAGATGCGAAAGCTCACCAGTAACCTGCGGATT GGCTTCGGGGCATTTGTGGACAAGCCTGTGTCACCATACATGTATATCTCCCCACCAGAG.

7. A nucleotide segment containing no more than 12,000 nucleotide base pairs including a sequence defining a structural gene coding for a polypeptide of 60 to 90 amino acid residues in length having a sequence homologous to the GPIIIa amino acid residue sequence represented by the formula:
DYPVDIYYLMDLSYSMKDDLWSIQNLGTKLATQMRKLTSNLRIGFGAGVDKPVSPYMYISPPE, wherein said structural gene sequence contains no more than 2,000 base pairs.

8. The nucleotide segment of claim 7 wherein said structural gene has a nucleotide base sequence represented by the formula:
GATTACCCTGTGGACATCTACTACTTGATGGACCTGTCTTACTCCATGAAGGATGATCTGTGGA GCATCCAGAACCTGGGTACCAAGCTGGCCACCCAGATGCGAAAGCTCACCAG-

TAACCTGCGGATT
GGCTTCGGGGCATTTGT-
GGACAAGCCTGTGTCACCATACATG-
TATATCTCCCCACCAGAG.

9. A monoclonal antibody comprising antibody molecules that immunoreact with a) a polypeptide according to claim 1, and b) the beta subunit of an Integrin to which the amino acid residue sequence of said polypeptide corresponds.

10. A monoclonal antibody comprising antibody molecules that immunoreact with a) GPIIIa, and b) a polypeptide corresponding to the formula:
DYPVDIYYLMDLSYSMKDDLWSIQNLGT-
KLATQMRKLTSNLRIGFGAFVDKPUS-
PYMYISPPE.

11. A monoclonal antibody comprising antibody molecules that immunoreact with a) the beta subunit of the LeuCam Integran and b) a polypeptide corresponding to the formula:
GYPIDLYYLMD-
LSYSMLDDLRNVKKLGGDLLRAL-
NEITESGRIGFGSFVDKTVLPFVNTHP.

12. A monoclonal antibody comprising antibody molecules that immunoreact with a) the beta subunit of the VLA Integran, and b) a polypeptide corresponding to the formula:
DYPIDLYYLMDLSYSMKD-
DLENVKSLGTDLMNEMRRITSD-
RFIGFGSFVEKTVMPYISTTP.

* * * * *

UNITED STATES PATENT AND TRADEMARK OFFICE
CERTIFICATE OF CORRECTION

PATENT NO. : 5,149,780
DATED : September 22, 1992
INVENTOR(S) : Plow, et al.

It is certified that error appears in the above-identified patent and that said Letters Patent is hereby corrected as shown below:

In Column 1, line 4, insert:

-- This invention was made with government support under Grant Nos. HL 16411 and HL 38292 awarded by the National Institutes of Health. The government has certain rights in the invention. --

Signed and Sealed this

Twenty-second Day of February, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO.   : 5,149,780
DATED        : September 22, 1992
INVENTOR(S)  : Edward F. Plow, Stanley E. D'Souza and Mark H. Ginsberg It is certified that error appears in the above-identified patent and that said Letters Patent is hereby corrected as shown below:

Column 1,
Line 5, insert:
-- This invention was made with government support under Grant Nos. HL 16411, HL 28235 and HL 38292 by the National Institutes of Health. The government may have certain rights in the invention. --

Signed and Sealed this

Seventh Day of May, 2002

Attest:

JAMES E. ROGAN
*Attesting Officer*     *Director of the United States Patent and Trademark Office*